United States Patent
Higuchi et al.

(10) Patent No.: US 7,208,631 B2
(45) Date of Patent: Apr. 24, 2007

(54) 2-ALKYLCYSTEINAMIDE OR SALT THEREOF, PROCESS FOR PRODUCING THESE, AND USE OF THESE

(75) Inventors: Yasushi Higuchi, Tokyo (JP); Akinori Tanaka, Niigata (JP); Ryuji Hasemi, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 5 days.

(21) Appl. No.: 10/552,634

(22) PCT Filed: Apr. 7, 2004

(86) PCT No.: PCT/JP2004/004988

§ 371 (c)(1),
(2), (4) Date: Oct. 7, 2005

(87) PCT Pub. No.: WO2004/090152

PCT Pub. Date: Oct. 21, 2004

(65) Prior Publication Data

US 2006/0287398 A1 Dec. 21, 2006

(30) Foreign Application Priority Data

Apr. 8, 2003 (JP) ............................. 2003-103898
Sep. 17, 2003 (JP) ............................. 2003-325057

(51) Int. Cl.
C07C 233/05 (2006.01)
C07C 231/10 (2006.01)

(52) U.S. Cl. ................ 564/193; 564/215; 435/29; 435/113; 435/129; 435/130; 435/280; 435/863; 435/910

(58) Field of Classification Search .............. 435/29, 435/113, 129, 130, 280, 863, 910; 564/193, 564/215
See application file for complete search history.

(56) References Cited

U.S. PATENT DOCUMENTS

| 4,440,788 A | 4/1984 | Terayama et al. |
| 4,585,892 A * | 4/1986 | Seebach et al. ............. 562/443 |
| 6,403,830 B2 * | 6/2002 | Webber et al. .............. 562/557 |
| 2003/0171597 A1 | 9/2003 | Katoh et al. |

FOREIGN PATENT DOCUMENTS

| JP | 57-14573 A | 1/1982 |
| JP | 2001-328970 A | 11/2001 |
| JP | 2002-315597 A | 10/2002 |

OTHER PUBLICATIONS

Brant, L., et al., "Thiazoline Ring Formation from 2-Methylcysteines and 2-Halomethylalanines," Heterocycles, vol. 58, pp. 601-634, 2002.

* cited by examiner

Primary Examiner—Shailendra Kumar
(74) Attorney, Agent, or Firm—Fitch, Even, Tabin & Flannery

(57) ABSTRACT

A process for producing a 2-alkylcysteinamide, which comprises hydrolysis of a 4-alkylthiazolidine-4-carboxamide represented by the general formula (2) or a salt thereof:

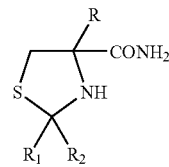

(2)

wherein R represents a lower alkyl group having 1–4 carbon atoms; and each of $R_1$ and $R_2$ independently represents hydrogen or a lower alkyl group having 1–4 carbon atoms, or $R_1$ and $R_2$ are linked together to form an alicyclic, structure having 4–7 carbon atoms, excluding the case where both $R_1$ and $R_2$ are hydrogen, to give a 2-alkylcysteinamide represented by the general formula (1) or a salt thereof

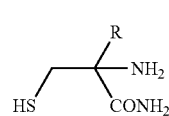

(1)

wherein R represents a lower alkyl group having 1–4 carbon atoms.

Cells of a microorganism or treated products thereof having activity of stereoselective hydrolysis of a 2-alkyl-L-cysteinamide are allowed to act on the compound represented by the general formula (1) to yield a 2-alkyl-L-cysteine.

7 Claims, No Drawings

2-ALKYLCYSTEINAMIDE OR SALT THEREOF, PROCESS FOR PRODUCING THESE, AND USE OF THESE

This Application is the National Phase of International Application No. PCT/JP2004/004988 filed Apr. 7, 2004, which designated the U.S. and was not published under PCT Article 21(2) in English, and this application claims, via the aforesaid International Application, the foreign priority benefit of and claims the priority from Japanese Application No. 2003-103898, filed Apr. 8, 2003, and from Japanese Application No. 2003-325057, filed Sep. 17, 2003, the complete disclosures of which are incorporated herein by reference.

TECHNICAL FIELD

The present invention relates to a 2-alkylcysteinamide represented by the later-shown general formula (1) or a salt thereof (hereinafter also simply referred to as a "2-alkylcysteinamide"), a process for producing the same, and use thereof. More specifically, it relates to a process for producing a 2-alkylcysteinamide represented by the later-shown general formula (1) through a hydrolysis of a 4-alkylthiazolidine-4-carboxamide represented by the later-shown general formula (2) or a salt thereof (hereinafter also simply referred to as a "4-alkylthiazolidine-4-carboxamide"). In addition, it also relates to the use of the above 2-alkylcysteinamide as a material for producing an optically active 2-alkylcysteine.

BACKGROUND ART

Conventionally, there have been publications describing a process for producing a 4-alkylthiozolidine-4-carboxamide represented by the later-shown general formula (2) (for example, refer to Justus Liebigs Ann. Chem. (1966), 697, 140–157). However, there is no description of a process for obtaining a 2-alkylcysteinamide represented by the later-shown general formula (1) from the 4-alkylthiozolidine-4-carboxamide. In addition, the above publication describes a technique for obtaining a cysteinamide derivative, penicillaminamide, by treating a 5,5-dimethylthiazolidine carboxamide in concentrated hydrochloric acid, however, when this technique is applied to the 4-alkylthiozolidine-4-carboxamide represented by the later-shown general formula (2), a hydrolysis is excessively proceeded, and a large amount of 2-alkylcysteine is generated as a by-product. Because of the generated 2-alkylcysteine that has properties similar to those of the 2-alkylcysteinamide of interest represented by the later-shown general formula (1), it makes separation and purification difficult. Accordingly, the above technique is not preferable.

Moreover, a conventional process for producing an optically active 2-alkyl-L-cysteine comprises, for example, providing an optically active L-cysteine methyl ester as a starting material; cyclizing it with pivalaldehyde; protecting the cyclized product with formaldehyde; methylating the protected product with a lithium reagent and methyl iodide; opening the ring with hydrochloric acid; and deprotecting it, to obtain a 2-methyl-L-cysteine in the form of a hydrochloric acid salt (see U.S. Pat. No. 6,403,830, for example). Nevertheless, this process requires an optically active substance as a starting material and a large number of steps, and thus is complicated. This process also requires expensive reagents. Thus, it is hardly said that this is an industrially excellent process.

There have been no reports regarding a process for producing the optically active 2-alkyl-L-cysteine represented by the later-shown general formula (2) through a stereoselective hydrolysis of a 2-alkylcysteinamide represented by the later-shown formula (1) using an enzyme derived from a microorganism.

DISCLOSURE OF THE INVENTION

It is an object of the present invention to solve the aforementioned problems of prior art techniques and to provide a process for producing an optically active 2-alkyl-L-cysteine that is useful as an intermediate for production of optically active pharmaceuticals, agricultural chemicals, or various types of industrial chemicals, in a small number of steps and at low cost.

As a result of intensive studies directed towards solving the above mentioned problems, the present inventors have found that the object can be achieved by providing a 2-alkylcysteinamide represented by the following general formula (1) or a salt thereof, and have completed the invention.

Thus, in accordance with one aspect of the present invention, there is provided a 2-alkylcysteinamide represented by the following general formula (1) or a salt thereof:

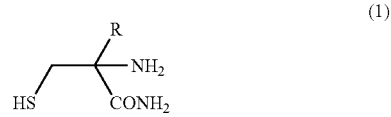
(1)

wherein R represents a lower alkyl group having 1–4 carbon atoms.

The 2-alkylcysteinamide represented by the general formula (1) has a mercapto group, an amino group, and a carboxylamide group in a molecule thereof, and thus is a compound which is expected to be widely used as a material for production of pharmaceuticals, agricultural chemicals, and various industrial chemicals. Thus, the 2-alkylcysteinamide is a novel compound which is very useful in the industry.

In addition, the 2-alkylcysteinamide represented by the general formula (1) can be produced at high yield using a 4-alkylthiazolidine-4-carboxamide represented by the following general formula (2) which is selectively hydrolyzed at a C—N bond in the thiazolidine ring.

Accordingly, in accordance with another aspect of the present invention, there is provided a process for producing a 2-alkylcysteinamide or a salt thereof through hydrolysis of a 4-alkylthiazolidine-4-carboxamide represented by the following general formula (2) or salt thereof to give a 2-alkylcysteinamide represented by the following general formula (1) or a salt thereof. If a 4-methylthiazolidine-4-carboxamide or a salt thereof wherein R represents methyl, is used in the above production process, a 2-methylcysteinamide or a salt thereof can efficiently be produced which can advantageously be used in the subsequent enzymatic reaction.

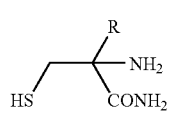

(1)

In the general formula (1), R represents a lower alkyl group having 1–4 carbon atoms.

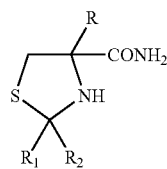

(2)

In the general formula (2), R represents a lower alkyl group having 1–4 carbon atoms; and each of $R_1$ and $R_2$ independently represents hydrogen or a lower alkyl group having 1–4 carbon atoms, or $R_1$ and $R_2$ are linked together to form an alicyclic structure having 4–7 carbon atoms, excluding the case where both $R_1$ and $R_2$ are hydrogen.

In the above production process, the 4-alkylthiazolidine-4-carboxamide represented by the general formula (2) or a salt thereof used as a raw material is preferably used in a form of an aqueous solution thereof, more preferably in a form of an aqueous solution of a mineral acid salt thereof.

Moreover, when the biochemical stereoselective hydrolysis of the 2-alkylcysteinamide represented by the general formula (1) is carried out by the action of cells of microorganism or treated products thereof having an activity of stereoselective hydrolysis of a 2-alkyl-L-cysteinamide, the 2-alkylcysteinamide can also be derivatized into an optically active 2-alkyl-L-cysteine that is also useful as an intermediate for production of pharmaceuticals, agricultural chemicals, and various industrial chemicals.

Accordingly, in accordance with still another aspect of the present invention, there is provided a process for producing an optically active 2-alkyl-L-cysteine, which is characterized by the production of a 2-alkly-L-cysteine represented by the general formula (1-L) from a 2-alkylcysteinamide represented by the general formula (1) by the action of cells of microorganism or treated products thereof having an activity of stereoselective hydrolysis of a 2-alkyl-L-cysteinamide.

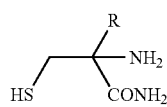

(1)

In the formula (1), R represents a lower alkyl group having 1–4 carbon atoms.

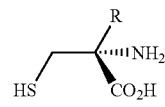

(1-L)

In the formula (1-L), R represents a lower alkyl group having 1–4 carbon atoms.

According to this production process, an optically active 2-alkyl-L-cysteine can be produced in a small number of steps at low cost.

In this production process, the microorganism having an activity of stereoselective hydrolysis of a 2-alkyl-L-cysteinamide is preferably a bacterium which belongs to the genus *Protaminobacter,* the genus *Mycoplana,* or the genus *Xanthobacter.*

In addition, in this production process, the stereoselective hydrolysis by the action of cells of microorganism or treated products thereof is preferably carried out under inert gas flow and/or in a coexistence of a reducing agent.

In this production process, compounds of the general formulas (1) and (1-L) wherein R represents methyl are advantageously used.

BEST MODE FOR CARRYING OUT THE INVENTION

Embodiments of the present invention will be described in detail below.

In the 2-alkylcysteinamide represented by the general formula (1) or a salt thereof of the present invention, R in the formula is not particularly limited, as long as it is a lower alkyl group having 1–4 carbon atoms including methyl group. Preferred examples of R may include linear or branched lower alkyl groups such as ethyl, propyl, isopropyl, butyl, isobutyl, sec-butyl, tert-butyl, as well as methyl. Of these, methyl is particularly preferable. In addition, the compound represented by the general formula (1) may form a salt, as well as a free form. Types of the salt are not particularly limited, as long as they are practically acceptable. Examples of the salt may include salts with inorganic acids such as hydrochloric acid and sulfuric acid, and salts with organic acids such as formic acid and acetic acid. Hydrochloride and sulfate are particularly preferable in terms of stability of the resulting 2-alkylcysteinamide or a salt thereof.

A 4-alkylthiazolidine-4-carboxamide represented by the general formula (2) or a salt thereof that is a material for production of the compound represented by the general formula (1) of the present invention can be produced as described below in accordance with the method described in a literature, Justus Liebigs Ann. Chem. (1966), 697, 140–157, etc.

1) A halogenated methyl alkyl ketone represented by the formula (3) shown below (wherein X represents a halogenated methyl group) and a carbonyl compound represented by the formula (4) shown below or an acetal (ketal) thereof are allowed to react with sodium hydrosulfide and ammonia, so as to obtain a thiazoline compound represented by the formula (5) shown below.

2) HCN is added to the obtained thiazoline represented by the formula (5) to obtain a nitrile represented by the formula (6) shown below.

3) The nitrile represented by the formula (6) is hydrolyzed with an acid catalyst to obtain a 4-alkylthiazolidine-4-carboxamide represented by the general formula (2) or its salt which is particularly shown below by the formula (2').

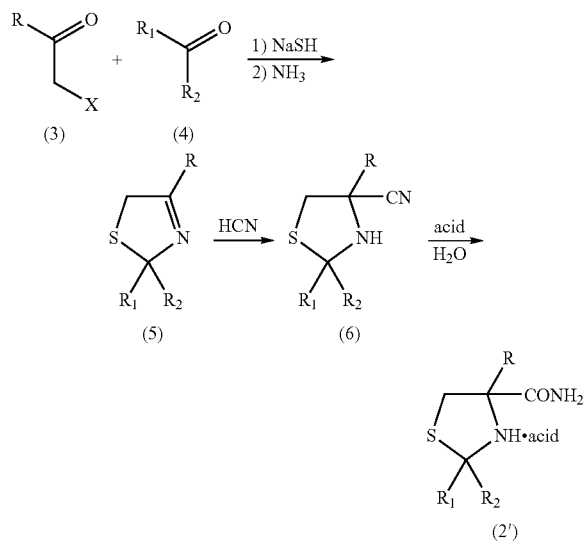

The 2-alkylcysteinamide represented by the general formula (1) or salt thereof can be produced by partial hydrolysis of the 4-alkylthiazolidine-4-carboxamide represented by the general formula (2) or a salt thereof. When the 4-alkylthiazolidine-4-carboxamide represented by the general formula (2) or a salt thereof is dissolved in pure water or a polar organic solvent containing water at an equivalent weight or more on heating, a hydrolytic ring-opening reaction progresses. This hydrolysis can be accelerated by addition of an acid catalyst. However, when an excessive amount of acid is present, a large amount of 2-alkylcysteine resulting from a further hydrolysis of the 2-alkylcysteinamide represented by the general formula (1) is unfavorably produced as a by-product. Thus, an acid catalyst is used at an equivalent ratio of preferably from 0.5 to 1.3, more preferably from 0.8 to 1.1, and most preferably 1 relative to the thiazolidine carboxamide represented by the general formula (2). Alternatively, the 2-alkylcysteinamide of interest represented by the general formula (1) can favorably be obtained by isolating and purifying the neutral salt represented by the formula (2') which consists of the thiazolidine carboxamide and an acid, and then heating it to reflux in pure water or a polar organic solvent containing water at an equivalent weight or more.

Types of the acid used as a catalyst are not particularly limited, as long as they are commonly used. Examples of the acid may include inorganic acids such as hydrochloric acid, sulfuric acid and phosphoric acid, and organic acids such as formic acid and acetic acid. Of these, inorganic acids such as hydrochloric acid and sulfuric acid are preferably used because of high reaction rate or favorable operability during purification. In this instance, the carbonyl compound represented by the formula (4) is dissociated as a result of the hydrolysis. By conducting such an operation as distillation during the reaction so as to remove the carbonyl compound from the reaction system, the reaction can be further efficiently carried out. The reaction quantitatively progresses, and only by eliminating the dissociated carbonyl compound represented by the formula (4) and a reaction solvent, the 2-alkylcysteinamide of interest represented by the general formula (1) or a salt thereof can be obtained at high yield and high purity.

The microorganism used for the biochemical stereoselective hydrolysis of the 2-alkylcysteinamide represented by the general formula (1) of the present invention is not particularly limited, as long as it has an activity of stereoselective hydrolysis of a 2-alkyl-L-cysteinamide corresponding to the 2-alkyl-L-cysteine of interest. Examples of such a microorganism may include those belonging to the genus *Protaminobacter,* the genus *Mycoplana,* the genus *Xanthobacter,* or the like. Specific examples thereof may include *Protaminobacter alboflavus* ATCC8458, *Mycoplana ramose* NCIB9440, *Mycoplana dimorpha* ATCC4279, *Xanthobacter autotrophicus* DSM597, and *Xanthobacter flavus* NCIB 10071, but are not limited thereto. In addition, both mutants induced from these microorganisms by artificial mutation procedures, and recombinants induced by genetic engineering procedures such as cell fusion and gene recombination, can be used in the present invention, as long as they have the aforementioned ability.

These microorganisms are generally cultured in a medium which contains a carbon source and a nitrogen source that can be generally assimilated, inorganic salts and nutrients essential for each microorganism, and so on. During the culture, the pH is preferably between 4 and 10, and the temperature is preferably between 20° C. and 50° C. The culture is aerobically carried out for 1 day to 1 week. The thus cultured microorganism can be used for the reaction in a form of a living cell mass or a processed product of the living cell mass, including a culture solution, an isolated cell mass, a crushed cell mass product, and a purified enzyme. Moreover, such a cell mass or enzyme may be immobilized in use according to an ordinary method.

Preferred conditions for the biochemical asymmetric hydrolysis reaction of the 2-alkylcysteinamide are as follows. The concentration of the 2-alkylcysteinamide is between 0.1% and 40% by weight. The amount of the cells of microorganism a treated products thereof to be used is 0.0001 to 3 times the 2-alkylcysteinamide on weight basis, in terms of dried microorganisms. The reaction temperature is between 10° C. and 70° C. The pH is between 4 and 13.

The 2-alkylcysteinamide as a reaction material and the 2-alkylcysteine as a product are likely to be oxidized. Thus, if these compounds are left in a presence of oxygen, they become a dimeric disulfide (2,2'-dialkylcystine). In order to prevent this, the biochemical stereoselective hydrolysis is preferably carried out in an atmosphere from which free oxygen or an oxygen donor is excluded. For example, the above reaction is preferably carried out, under inert gas flow such as of nitrogen and argon, or under conditions wherein a reducing agent acting as an oxygen scavenger, such as 2-mercaptoethanol, is allowed to coexist in the reaction system.

The optically active 2-alkyl-L-cysteine resulting from the biochemical stereoselective hydrolysis of the 2-alkylcysteinamide can be obtained by removing the cells of microorganisms from a reaction mixture by conventional solid-liquid separation means such as centrifugation and filtration with a filtration membrane, adjusting the obtained solution to pH 4 to pH 7 followed by concentration, cooling the concentrate, and separating the resultant crystallized crystals by filtration. In addition, as necessary, the concentration may be carried out after the solution has been treated by adding thereto an adsorbent such as an activated charcoal. Otherwise, the concentrate of the solution may be supplemented with and redissolved in a water-soluble organic solvent including alcohols such as methanol, ethanol, and propanol, ketones such as acetone, ethers such as tetrahydrofuran and dioxane, mixed solvents containing these solvents in combination and optionally water, followed by cooling and crystallization, so that a 2-alkylcysteine can conveniently be obtained.

As stated above, an optically active 2-alkyl-L-cysteine such as a 2-methyl-L-cysteine and a 2-ethyl-L-cysteine can be produced.

EXAMPLES

The present invention will be more specifically described with reference to the following examples. However, these examples are not intended to limit the scope of the present invention.

Example 1

1) Preparation of 2,2,4-trimethylthiazoline 250 g of sodium hydrosulfide (purity: 70%) was dissolved in 500 mL of water, and while stirring, the mixture was then cooled to 5° C. in an ice bath. Thereafter, 278 g of chloroacetone was slowly dropped thereinto. After completion of such dropping, the mixture was returned to a room temperature in a water bath. Thereafter, 261 g of acetone was added thereto, and 800 mL of methylene chloride was then added thereto. While the mixture was controlled in a water bath such that the internal temperature did not exceed 30° C., 616 g of 25% ammonia water was slowly dropped thereinto. After completion of such dropping, the mixture was stirred for 4 hours. The reaction solution was then separated, and an organic layer was washed with a saturated saline solution once, and then with pure water twice. Thereafter, anhydrous sodium sulfate was added to the organic layer, and the mixture was then stirred for 3 hours, followed by dehydration and drying. The solid was separated by filtration, and the filtrate was distilled off under reduced pressure. 290 g (74.8 mol %) of 2,2,4-trimethylthiazoline was obtained.

2) Preparation of 2,2,4-trimethyl-4-cyanothiazolidine 317 g of 2,2,4-trimethylthiazoline was dissolved in 500 mL of diethyl ether, and the mixture was adjusted to 15° C. Under stirring, the obtained solution was slowly bubbled with 132.7 g of hydrocyanic acid gas, while the temperature was kept below 20° C. After the completion of the blowing of hydrocyanic acid gas, the mixture was continuously stirred for 3 hours while the temperature was kept at 20° C. The pressure of the reaction solution was then reduced with an aspirator, and diethyl ether was distilled off to obtain a white solid. The obtained white solid was dissolved in a mixed solvent (diethyl ether/hexane=800 mL/350 mL), and the obtained solution was cooled to −50° C. The precipitated crystals were separated by filtration. The filtrate was further concentrated, and the further precipitated crystals were separated by filtration. 384 g (83 mol%) of 2,2,4-trimethyl-4-cyanothiazolidine was obtained in total.

3) Preparation of 2,2,4-trimethylthiazolidine-4-carboxamide and hydrochloride thereof 1,924 g of concentrated hydrochloric acid (36%) was stirred, while the temperature was kept at 20° C. or lower.

258 g of 2,2,4-trimethyl-4-cyanothiazolidine was slowly added thereto. The mixture was warmed to 25° C. and then stirred for 13 hours. Thereafter, the precipitated crystals were separated by filtration, and then washed with diethyl ether, followed by drying under reduced pressure, to obtain 97 g (46 mol %) of 2,2,4-trimethylthiazolidine-4-carboxamide hydrochloride. Thereafter, the filtrate obtained after the filtration of the crystals was cooled in an ice bath. While stirring, 1,228 g of 25% aqueous ammonia solution was slowly added dropwise thereto. The precipitated crystals were separated by filtration and were then washed with 800 mL of pure water. 67 g (38 mol %) of 2,2,4-trimethylthiazolidine-4-carboxamide was obtained.

4) Preparation of 2-methylcysteinamide hydrochloride 90 g of 2,2,4-trimethylthiazolidine-4-carboxamide hydrochloride obtained as described above was dissolved in 1 L of pure water. The obtained solution was heated in a vessel equipped with a distillation column using an oil bath at 105° C. The reaction was carried out for 3 hours, while the distillate was slowly removed from the top of the distillation column. Thereafter, the reaction solution was concentrated and then dried under reduced pressure. 77 g (96 mol %) of 2-methylcysteinamide hydrochloride in the form of a colorless vitreous solid was obtained.

5) Results of analysis of 2-methylcysteinamide hydrochloride

The results obtained by analyzing the properties of the obtained 2-methylcysteinamide hydrochloride are shown below.

2-methylcysteinamide hydrochloride; colorless vitreous solid (deliquescent)
$^1$H-NMR (90 MHz, $D_2O$) δ [ppm] 3.19 (1H, d, J15.3 Hz), 2.95 (1H, d, J15.3 Hz), 1.64 (3H, s)
$^{13}$C-NMR (22.6 MHz, $D_2O$) δ [ppm] 173.78(s), 62.31(s), 31.73(t), 22.21(q)
IR [cm-1] (KBr) 1703, 1624, 1574, 1506, 1377, 1279, 1230, 1124
elemental analysis (measurements) C, 28.01; H, 6.60; N, 16.33; S, 18.72; Cl, 20.75; (calculation) C, 28.15; H, 6.50; N, 16.41; O, 9.37; S, 18.79; Cl, 20.77.

Example 2

A medium with the composition described below was prepared. 200 mL of the medium was placed in a 1-liter Erlenmeyer flask. After the medium had been sterilized, it was inoculated with *Xanthobacter flavus* NCIB 10071. The obtained mixture was subjected to a shaking culture at 30° C. for 48 hours.

| Medium composition (pH 7.0) | |
|---|---|
| Glucose | 10 g |
| Polypeptone | 5 g |
| Yeast extract | 5 g |
| $KH_2PO_4$ | 1 g |
| $MgSO_4/7H_2O$ | 0.4 g |
| $FeSO_4/7H_2O$ | 0.01 g |
| $MnCl_2/4H_2O$ | 0.01 g |
| Water | 1 L |

Subsequently, intact cells equivalent to 1.0 g of dried cells were obtained from the culture solution by centrifugation. 10.0 g (0.06 mol) of the 2-methylcysteinamide hydrochloride produced in Example 1 was dissolved in 300 mL of a 50 mM phosphate buffer. The obtained solution was placed in a 500-mL flask, and the strain corresponding to 1.0 g of dried microorganisms was then added thereto. The obtained mixture was stirred at 30° C. for 24 hours under nitrogen flow, so as to carry out hydrolysis.

After completion of the reaction, the cells of microorganism were removed from the reaction solution by centrifugation to obtain a supernatant. After deaeration, the supernatant was supplemented with 2 g of activated charcoal that had previously been subjected to inert gas substitution, and the mixture was stirred for 2 hours. Thereafter, the activated carbon was removed by filtration, and water was then distilled off under reduced pressure using an evaporator to obtain a white paste-like solid. 20 mL of isopropanol was added to the paste-like concentrate, and the mixture was then heated while stirring. Thereafter, the mixture was left to stand at 5° C. overnight. Thereafter, the precipitated crystals were collected by filtration. The thus filtrated crystals were recrystallized from ethanol to obtain 2.6 g (0.02 mol) of 2-methyl-L-cysteine. The yield of isolation was found to be 76 mol % relative to 2-methyl-L-cysteinamide contained in the racemic mixture that had been used for the reaction, and was found to be 38 mol % relative to the racemic mixture including 2-methyl-L-cysteinamide. Moreover, this solid was analyzed by liquid chromatography using an optical isomer separation column. As a result, the optical purify was found to be 98% e.e. or more.

Example 3

Various microorganisms were cultured in the same manner as in Example 2, to obtain intact cell. In the same manner as in Example 2, enzymatic reaction was carried out using 10 g (0.06 mol) of 2-methylcysteinamide as a substrate and the above various strains of microorganisms, and supernatants from which the cells of microorganism had been removed were then analyzed by liquid chromatography. The results are shown in Table 1. As a result of the analysis of the above supernatants by liquid chromatography using optical isomer separation columns, the optical purity was found to be 90% e.e. or more in all cases.

The details of the codes used in Table 1 are as follows.

Yield 1: the yield of 2-methyl-L-cysteine (mol %) based on 2-methylcysteinamide contained in the racemic mixture.

Yield 2: the yield of 2-methyl-L-cysteine (mol %) based on 2-methyl-L-cysteinamide contained in the racemic mixture Intact cell 1: *Protaminobacter alboflavus* ATCC8458.
Intact cell 2: *Mycoplana ramose* NCIB9440.
Intact cell 3: *Mycoplana dimorpha* ATCC 4279.
Intact cell 4: *Xanthobacter autotrophicus* DSM597.

TABLE 1

| Intact cell | Yield 1 | Yield 2 | Optical purity (e.e. %) |
|---|---|---|---|
| Intact cell 1 | 29 | 58 | 91.2 |
| Intact cell 2 | 32 | 65 | 90.0 |
| Intact cell 3 | 25 | 50 | 93.8 |
| Intact cell 4 | 37 | 74 | 98.2 |

INDUSTRIAL APPLICABILITY

The 2-alkylcysteinamide, which is represented by the general formula (1) and produced by the present invention, is expected to be used widely as a production material for pharmaceuticals, agricultural chemicals, and various industrial chemicals, and thus is extremely useful for development of the industry. In addition, it is also useful as a material for an optically active 2-alkyl-L-cysteine represented by the general formula (1-L).

The present process for producing a 2-methyl-L-cysteine through the stereoselective hydrolysis of 2-alkylcysteinamide represented by the general formula (1), that is a racemic mixture, by the action of the cells of microorganism or treated products thereof having an activity of stereoselective hydrolysis of a 2-alkyl-L-cysteinamide, enables inexpensive production of an optically active 2-alkyl-L-cysteine that is an extremely important intermediate for production of pharmaceuticals, agricultural chemicals, and various industrial chemicals, in a small number of steps. Thus, this production process greatly contributes to development of the industry.

The invention claimed is:

1. A 2-alkylcysteinamide represented by the general formula (1) or a salt thereof:

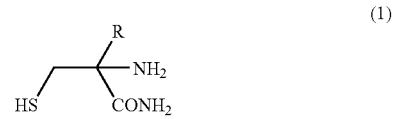

(1)

wherein R represents a lower alkyl group having 1–4 carbon atoms.

2. A process for producing a 2-alkylcysteinamide or a salt thereof through a hydrolysis of a 4-alkylthiazolidine-4-carboxamide represented by the general formula (2) or salt thereof:

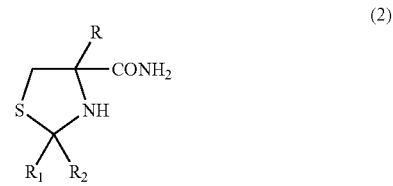

(2)

wherein R represents a lower alkyl group having 1–4 carbon atoms; and each of $R_1$ and $R_2$ independently represents hydrogen or a lower alkyl group having 1–4 carbon atoms, or $R_1$ and $R_2$ are linked together to form an alicyclic structure having 4–7 carbon atoms, excluding the case where both $R_1$ and $R_2$ are hydrogen, to give a 2-alkylcysteinamide represented by the general formula (1) or a salt thereof

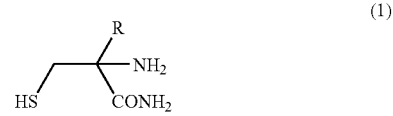

(1)

wherein R represents a lower alkyl group having 1–4 carbon atoms.

3. The process for producing a 2-alkylcysteinamide or a salt thereof according to claim 2, wherein an aqueous solution of a 4-alkylthiazolidine-4-carboxamide or a salt thereof is used as the 4-alkylthiazolidine-4-carboxamide represented by the general formula (2) or a salt thereof.

4. A process for producing an optically active 2-alkyl-L-cysteine, which is characterized in that it comprises allowing cells of a microorganism or a treated product thereof having an activity of stereoselectively hydrolyzing a 2-alkyl-L-cysteinamide to act on a 2-alkylcysteinamide represented by the general formula (1),

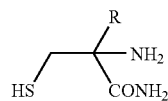
(1)

wherein R represents a lower alkyl group having 1–4 carbon atoms, to produce a 2-alkyl-L-cysteine represented by the general formula (1-L):

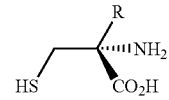
(1-L)

wherein R represents a lower alkyl group having 1–4 carbon atoms.

5. The process for producing an optically active 2-alkyl-L-cysteine according to claim 4, wherein the microorganism having an activity of stereoselective hydrolysis for a 2-alkyl-L-cysteinamide is a bacterium which belongs to the genus *Protaminobacter,* the genus *Mycoplana,* or the genus *Xanthobacter.*

6. The process for producing an optically active 2-alkyl-L-cysteine according to claim 4, wherein the stereoselective hydrolysis by the action of cells of a microorganism and/or a treated product thereof is carried out under inert gas flow and/or in a coexistence of a reducing agent.

7. The process for producing an optically active 2-alkyl-L-cysteine according to claim 4, wherein R represents methyl in the general formulas (1) and (1-L).

* * * * *